United States Patent [19]

Caplan et al.

[11] Patent Number: 6,010,696
[45] Date of Patent: *Jan. 4, 2000

[54] ENHANCING HEMATOPOIETIC PROGENITOR CELL ENGRAFTMENT USING MESENCHYMAL STEM CELLS

[75] Inventors: Arnold I. Caplan; Stephen E. Haynesworth, both of Cleveland Heights; Stanton L. Gerson, Pepper Pike; Hillard M. Lazarus, Shaker Heights, all of Ohio

[73] Assignee: Osiris Therapeutics, Inc., Baltimore, Md.

[ * ] Notice: This patent is subject to a terminal disclaimer.

[21] Appl. No.: 09/047,950

[22] Filed: Mar. 25, 1998

Related U.S. Application Data

[63] Continuation-in-part of application No. 08/377,771, Jan. 24, 1995, Pat. No. 5,733,542, which is a continuation-in-part of application No. 08/193,262, Feb. 8, 1994, Pat. No. 5,486,359, which is a continuation-in-part of application No. 08/034,272, Mar. 22, 1993, abandoned, which is a continuation-in-part of application No. 07/716,917, Jun. 18, 1991, abandoned, which is a continuation-in-part of application No. 07/615,430, Nov. 16, 1990, abandoned, and a continuation-in-part of application No. 08/038,517, Mar. 29, 1993, abandoned, which is a division of application No. 07/614,912, Nov. 16, 1990, Pat. No. 5,226,914, and a continuation-in-part of application No. 08/038,512, Mar. 29, 1993, abandoned, which is a division of application No. 07/614,915, Nov. 16, 1990, Pat. No. 5,197,985.

[51] Int. Cl.[7] .............................. C12N 5/00; A61K 35/28; A61F 13/00
[52] U.S. Cl. ......................... 424/93.7; 424/422; 424/423; 424/548; 424/549; 424/577; 435/325; 435/366; 435/372; 435/373; 435/372.1; 435/372.2; 435/372.3; 435/377
[58] Field of Search .................................. 424/93.7, 422, 424/423, 548, 549, 577; 435/325, 366, 372, 373, 372.1–372.3, 377

[56] References Cited

U.S. PATENT DOCUMENTS

| | | | |
|---|---|---|---|
| 3,968,567 | 7/1976 | Nevins | 32/15 |
| 4,430,760 | 2/1984 | Smestad | 3/1.9 |
| 4,596,574 | 6/1986 | Urist | 623/16 |
| 4,642,120 | 2/1987 | Nevo et al. | 623/16 |
| 4,714,680 | 12/1987 | Civin | 435/240.25 |
| 4,721,096 | 1/1988 | Naughton et al. | 128/1 R |
| 5,061,620 | 10/1991 | Tsukamoto et al. | 435/7.21 |
| 5,087,570 | 2/1992 | Weissman et al. | 4244/93.7 |
| 5,206,023 | 4/1993 | Hunziker | 424/423 |
| 5,256,560 | 10/1993 | Lawman et al. | 435/325 |
| 5,733,542 | 3/1998 | Haynesworth et al. | 424/93.7 |

OTHER PUBLICATIONS

Dicke et al. Lancet, vol. 1, 8115, pp. 514–517, (1979).
Franzen et al., Differentiation, 36:199–210 (1987).
Goshima et al., Clin. Orthop. & Rel. Res., 269: 274–283 (1991).
Goshima et al., Clin. Orthop. 262: 298–311 (1991).
Nakahara et al., J. Orthop. Res., 9:465–476.
Linsenmeyer et al., Biochem. Biophys. Res. Comm., 92 (2): 440–446 (1980).
Ashton et al., Calcif. Tissue Int., 36:83–86 (1984).
Bruder et al., Bone and Mineral, 11: 141–151 (1990).
Goding et al., Monoclonal Antibodies: Principles and Practice, Academic Press (NY), pages 56–97(1983).
Kipps et al., in Weir (Ed), Handbook of Expt'l Immunol, Blackwell Scientiic Publ. (London), vol. 4, pp. 108.1–108.9 (1986).
Harlow et al., Antibodies: a Laboratory Manual (vol. 4), Cold Spring Harbour, pp. 153–154, 392–393 and 578–581 (1988).
Lazarus et al.,*ASBMT Abstract* (*unpub.*), Jan. 26, 1995.

*Primary Examiner*—Leon B. Lankford, Jr.
*Assistant Examiner*—Christopher R. Tate
*Attorney, Agent, or Firm*—Elliot M. Olstein

[57] ABSTRACT

Method and preparations for enhancing hematopoietic progenitor cell engraftment in an individual by administering (i) a culturally expanded mesenchymal stem cell preparation and (ii) hematopoietic progenitor cells. The mesenchymal stem cells are administered in an amount effective to promote engraftment of the hematopoietic progenitor cells.

8 Claims, No Drawings

ENHANCING HEMATOPOIETIC PROGENITOR CELL ENGRAFTMENT USING MESENCHYMAL STEM CELLS

This is a continuation-in-part of U.S. Ser. No. 08/377,771 filed Jan. 24, 1995 (U.S. Pat. No. 5,733,542 issued on Mar. 31, 1998); which is a continuation-in-part of U.S. Ser. No. 08/193,262, filed Feb. 8, 1994 (U.S. Pat. No. 5,486,359 issued on Jan. 23, 1996); which is a continuation-in-part of U.S. Ser. No. 08/034,272, filed Mar. 22, 1993 (abandoned); which is a continuation-in-part of U.S. Ser. No. 07/716,917 filed Jun. 18, 1991 (abandoned); which is a continuation-in-part of U.S. Ser. No. 07/615,430 filed Nov. 16, 1990 (abandoned) and a continuation-in-part of U.S. Ser. No. 08/038,517, filed Mar. 29, 1993 (abandoned); which is a divisional of U.S. Ser. No. 07/614,912, filed Nov. 16, 1990 (U.S. Pat. No. 5,226,914 issued on Jul. 13, 1993) and a continuation-in-part of U.S. Ser. No. 08/038,512, filed Mar. 29, 1993 (abandoned); which is a divisional of Ser. No. 07/614,915, filed Nov. 16, 1990 (U.S. Pat. No. 5,197,985 issued on Mar. 30, 1993).

The present invention is directed to various methods and devices for using mesenchymal stem cells (mesenchymal stem cells) to enhance hematopoietic progenitor cell engraftment. Mesenchymal stem cells are the formative pluripotent blast cells found in the bone that are capable of differentiating into any of the specific types of connective tissues (i.e., the tissues of the adipose, areolar, osseous, cartilaginous, elastic, and fibrous connective tissues) depending upon various environmental influences. Although these cells are normally present at very low frequencies in bone marrow and other mesenchymal tissues, the inventors of the present invention have discovered a process for isolating, purifying, and greatly replicating the mesenchymal stem cells in culture, i.e. in vitro. This discovery is the subject of U.S. Pat. No. 5,486,359 issued Jan. 23, 1996. The methods and devices of the invention utilize such isolated and culture-expanded mesenchymal stem cells. Under selected conditions, they can be induced to differentiate into different types of skeletal and connective tissues such as bone, cartilage, tendon, ligament, muscle, other connective tissues and marrow stroma.

The marrow stroma provides the scaffolding as well as soluble factors which direct and support blood cell synthesis, i.e., hematopoiesis. The present invention is directed to a method to improve the process of hematopoietic progenitor cell transplantation which is used to regenerate blood cells and marrow tissue in patients where their marrow is depleted or destroyed, such as, for example, during intensive radiation and chemotherapy treatment. Along this line, the inventors have discovered that after lethal doses of radiation, culture-expanded mesenchymal stem cells can increase survival and decrease the time of blood and marrow cell regeneration when transplanted with hematopoietic progenitor cells.

The present invention provides a method for enhancing the regeneration of marrow tissue through improved hematopoietic progenitor cell transplantation using mesenchymal stem cells. The hematopoietic cells may be derived from the bone marrow or from peripheral blood, with such a procedure generally being referred to in the art as bone marrow transplantation. The method for enhancing hematopoietic progenitor cell engraftment comprises administering to an individual in need thereof, (i) mesenchymal stem cells and (ii) hematopoietic progenitor cells, wherein said mesenchymal stem cells are administered in an amount effective to promote engraftment of the hematopoietic progenitor cells in the individual. More particularly, one embodiment of the invention is directed to a method for using a culture medium comprised of Dulbecco's Modified Essential Medium with low glucose (DMEM-LG) or medium 199 plus 1% human albumin as a vehicle or carrier for mesenchymal stem cells which, when administered systemically, will migrate, or home, to the marrow cavity and differentiate into marrow stroma, thereby regenerating the marrow stroma. The mesenchymal stem cells can be administered systemically, e.g., intravenously, into various delivery sites or directly into the bone.

A further aspect of the present invention is directed to the timing of injection of the mesenchymal stem cells into the patient relative to injection of the hematopoietic progenitor cells. In one embodiment, the mesenchymal stem cells are injected simultaneously with the hematopoietic progenitor cells. In another embodiment, the mesenchymal stem cells are administered before or after the injection of the hematopoietic progenitor cells.

The present invention is useful to enhance the effectiveness of hematopoietic progenitor cell engraftment as a treatment for cancer. The treatment of cancer by x-irradiation or alkylating therapy destroys the bone marrow microenvironment as well as the hematopoietic stem cells. The current treatment is to transplant the patient after marrow ablation with hematopoietic progenitor cells which have been previously harvested and cryopreserved. However, because the bone marrow microenvironment is destroyed, hematopoietic progenitor cell engraftment is delayed until the stromal environment is restored. As a result, a critical aspect of the present invention is directed to the advantages of transplanting isolated, purified, culture-expanded mesenchymal stem cells to accelerate the process of stromal reconstitution and ultimately marrow engraftment.

Modes of administration of the mesenchymal stem cell preparation include but are not limited to systemic intravenous injection and injection directly to the intended site of activity. The preparation can be administered by any convenient route, for example by infusion or bolus injection and can be administered together with other biologically active agents. Administration is preferably systemic.

The present invention also provides pharmaceutical compositions. Such compositions comprise a therapeutically effective amount of the mesenchymal stem cells, and a pharmaceutically acceptable carrier or excipient. Such a carrier includes but is not limited to medium 199 plus 1% serum albumin, saline, buffered saline, dextrose, water, and combinations thereof The formulation should suit the mode of administration.

In a preferred embodiment, the mesenchymal stem cell preparation or composition is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The method of the invention can be altered, particularly by (1) increasing or decreasing the time interval between injecting mesenchymal stem cells and injecting the hematopoietic progenitor cells; (2) increasing or decreasing the amount of mesenchymal stem cells injected; (3) varying the number of mesenchymal stem cell injections; (4) varying the method of delivery of mesenchymal stem cells; or (5) varying the source of mesenchymal stem cells. Although mesenchymal stem cells derived from the tissue donor is preferable, the mesenchymal stem cells can be obtained from other individuals or species, or from genetically-engineered inbred donor strains, or from in vitro cell culture.

The mesenchymal stem cell preparation is used in an amount effective to promote engraftment of hematopoietic progenitor cells in the recipient. In general, such amount is at least $1 \times 10^4$ mesenchymal stem cells per kg of body weight and most generally need not be more than $7 \times 10^5$ mesenchymal stem cells/kg. Preferably, it is at least about $2 \times 10^5$ mesenchymal stem cells/kg prior to hematopoietic progenitor cell introduction and usually need not be more than about $7 \times 10^5$ mesenchymal stem cells/kg. The mesenchymal stem cell preparation may be administered concurrently with the hematopoietic progenitor cells or for a period prior to hematopoietic progenitor cell introduction of at least about 7 days but generally not to exceed 30 days, with a typical therapeutic treatment period of 7 to 14 days. The mesenchymal stem cell preparation preferably is administered either intravenously one to three times per day, and may be adjusted to meet optimal efficacy and pharmacological dosing.

The invention also provides a pharmaceutical pack or kit comprising one or more containers filled with one or more of the ingredients of the pharmaceutical preparation of the invention. Associated with such container(s) can be a notice in the form prescribed by a governmental agency regulating the manufacture, use or sale of pharmaceuticals or biological products, which notice reflects approval by the agency of manufacture, use or sale for human administration.

EXAMPLE 1

Isolation, Purification and Cultural Expansion of Marrow-Derived Mesenchymal Stem Cells Marrow in femoral head cancellous bone pieces was obtained from patients with degenerative joint disease during hip or knee joint replacement surgery. In addition, marrow was also obtained by iliac aspirate from normal donors and oncology patients who were having marrow harvested for future bone marrow transplantation. All of the oncology patients had malignancies unrelated to the stromal cells and the stromal cells expressed normal karyotype.

Marrow for cell culture was prepared from plugs of cancellous bone marrow as follows. Plugs of cancellous bone marrow (0.5–1.5 ml) were transferred to sterile tubes to which 25 ml Dulbecco's Modified Eagles Medium with low glucose (DMEM-LG) (GIBCO, Grand Island, N.Y.) with selected batches of 10% fetal bovine serum (complete medium) was added. The tubes were vortexed to disperse the marrow, then spun at 1000 rpm for 5 minutes to pellet cells and bone pieces. The supernatant and fat layer were removed and the marrow and bone were reconstituted in 5 ml complete medium and vortexed to suspend the marrow cells. The suspended cells were collected with a 10 ml syringe fitted with a 16 gauge needle and transferred to separate tubes. Bone pieces were reconstituted in 5 ml of complete medium and the marrow cells were collected as before. Collection of marrow cells was considered complete when a pellet of yellowish-white cancellous bone pieces was all that remained in the original tube. Marrow cells were separated into a single cell suspension by passing them through syringes fitted with 18 and 20 gauge needles. Cells were spun at 1000×g for 5 minutes after which the fat layer and supernatant were removed. Cells were reconstituted in complete medium, counted with a hemocytometer (red blood cells were lysed prior to counting with 4% acetic acid), and plated in 100 mm dishes at $50 \times 10^6$ nucleated cells/dish.

Marrow for cell culture was prepared from aspirated bone marrow as follows. Aspirate marrow (5–10 ml) was transferred to sterile 50 ml plastic centrifuge tubes to which 20 ml complete medium was added. The tubes were spun at 1,500 rpm for 5 minutes to pellet the cells. The supernatant and fat layer were removed and the cell pellets were resuspended to 5 ml with complete medium. The cell suspensions then were loaded onto 70% Percoll (Sigma, St. Louis, Mo.) gradients with a 10 ml pipette and spun at 2,000 rpm (460×g) in a GS34 rotor for 15 minutes. In order to harvest the cells, the tube is marked just below the high concentrated band of platelets, about 25% to 35% of the way down the tube. (Pooled density=1.03 g/ml.) Using a 10 ml pipette, the medium is aspirated off from the top down to the marked line (approximately 12–14 ml). The collected fraction is transferred to a 50 ml conical plastic tube. 30 ml of complete medium then is added to the tube and centrifuged for 5 minutes at 1,500 rpm. The supernatant then is removed and discarded.

The cells then are resuspended in 7 ml of complete medium, and a uniform cell suspension is generated by pipetting cells up and down with a 10 ml pipette. The cells are counted by taking 20 µl of uniform cell suspension, and adding 20 µl of 4% acetic acid to the cell suspension. The suspension is mixed and transferred to a hemocytometer, and the cells are counted.

Cell concentration then is adjusted with complete medium to $50 \times 10^6$ cells per 7 ml. 7 ml of cells ($50 \times 10^6$ cells) then are plated per 100 mm culture plate.

The marrow mesenchymal stem cells were purified and expanded as follows. Marrow cells from either the femoral head cancellous bone or the iliac aspirate were cultured in complete medium (i.e., DMEM-LG medium with 10% fetal bovine serum) at 37° C. in humidified atmosphere containing 95% air and 5% $CO_2$. On day 3 after plating, nonadherent cells were removed from the cultures by aspirating the original medium from the plates and replacing the original medium with 7 ml of fresh complete medium. Subsequent medium changes were performed every 3 to 4 days. This process of removing the non-adherent cells during culture media changes results in purification of the mesenchymal stem cells which selectively adhere to the culture plates. When primary culture dishes became nearly confluent, the medium was removed and each plate rinsed with 7 ml of sterile Tyrode's solution. The cells were detached with 4 ml of 0.25% trypsin with 0.1 mM EDTA (GIBCO) for 5 minutes at 37° C. The action of trypsin was stopped with 2 ml of calf serum. The cells then were collected with a 10 ml pipette and centrifuged for 5 minutes at 1,500 rpm. The supernatant then is removed, and the cells resuspended from each plate in 21 ml complete medium, and a uniform cell suspension is generated by gently pipetting the cells up and down in the pipette. The cells from each culture then are counted and plated in three new 100 ml plates in 7 ml complete medium. The three new plates of cells are termed first passage cultures. First passage cells then were allowed to expand until they became near confluent and were then replated as described above to create second passage cultures. At each passage, aliquots of cells were cryopreserved in 90% fetal bovine serum with 10% DMSO (freezing medium).

EXAMPLE 2

Mesenchymal stem cells were obtained from 10 ml of autologous human bone marrow collected either at the time of autologous bone marrow harvest, or during a routine diagnostic bone marrow examination, from the iliac crest. These mesenchymal stem cells were culture expanded and infused into 14 patients who had hematologic malignancies, but had no evidence of active malignancy, and had not received chemotherapy or radiation therapy for at least 4 weeks before collection of mesenchymal stem cells. Five patients each received 1 million autologous mesenchymal stem cells, five patients each were given 10 million mesenchymal stem cells, and four patients each received 50 million mesenchymal stem cells. Toxicity for each patient was determined according to the National Cancer Institute toxicity grading scale. The toxicity grading scale was the same as that based upon the common toxicity criteria for a Phase II trial of high-dose sequential chemotherapy and peripheral blood stem cell autologous transplantation as initial therapy for patients with poor prognosis non-Hodgkin's lymphoma. (National Cancer Institute document, draft 4/94: E2493.) Toxicity was graded on a scale from 0 to 4. No Grade 2 or greater toxic effects were observed, and in two patients that received 10 million mesenchymal stem cells, there appeared to be an increase in bone marrow cellularity.

EXAMPLE 3

Administration of Bone Marrow Cells and Mesenchymal Stem Cells to Breast Cancer Patients Treated with Chemotherapy A breast cancer patient undergoes a diagnostic posterior iliac crest bone marrow aspiration and biopsy using a local anesthetic. A small portion (2 to 3 ml) of the aliquot (10 to 20 ml) of marrow is submitted for routine histologic testing and determination of tumor content using immunoperoxidase testing of cells grown in semisolid agar as described in Ross, et al., *Blood.*, Vol. 82, pgs. 2605–2610 (1993). The remainder of the cells are cultured as hereinabove described. After at least 3 weeks in culture, samples of the mesenchymal stem cells are submitted for cell counting, cell viability (Trypan Blue), and cell surface immunophenotyping (testing with monoclonal antibodies SH2, SH3, and SH4). SH2 is produced by a hybridoma cell line assigned ATCC Accession No. HB10743. SH3 is produced by a hybridoma cell line assigned ATCC Accession No. HB10744. SH4 is produced by a hybridoma cell line assigned ATCC Accession No. HB10745. Samples also are submitted for detection of occult breast cancer.

The patient also undergoes placement of a pheresis central venous catheter, and receives subcutaneous injections of G-CSF (filgrastin) 10 $\mu$g/kg/day as described in Peters, et al., *Blood*, Vol. 81, pgs. 1709–1719 (1993); Chao, et al., *Blood*, Vol. 81, pgs. 2031–2035 (1993); Sheridan, et al., *The Lancet*, Vol. 2, pgs. 891–895 (1989); and Winter, et al., *Blood*, Vol. 82, pg. 293a (1993). G-CSF injections begin at least 3 days before the first pheresis is initiated. G-CSF therapy is withheld if the white blood cell count rises above 40,000/$\mu$L and is resumed once the white blood cell count drops to less than 20,000/$\mu$L.

If the patient is receiving only G-CSF as the vehicle for "mobilization" of peripheral blood progenitor cells, the patient must not have received chemotherapy within 4 weeks of the planned pheresis. If the patient has received both conventional chemotherapy and G-CSF treatment for mobilization, the patient must not have received chemotherapy within 10 days of the planned pheresis, and the white blood cell count must be at least 800/$\mu$L and the platelet count at least 30,000/$\mu$L.

Daily pheresis procedures are performed using a Cobe Spectra instrument (Cobe, Lakewood, Colo.), and each cellular collection is cryopreserved using a controlled-rate liquid nitrogen freezer, until at least $15\times10^8$ mononuclear cells/kg are collected—(Lazarus, et al., *Bone Marrow Transplant*, Vol. 7, pgs. 241–246 (1991)). Each peripheral blood progenitor cell will be processed and cryopreserved according to previously published techniques. (Lazarus, et al., *J. Clin, Oncol.*, Vol. 10, pgs, 1682–1689) (1992); Lazarus et al., (1991)).

Eight days before the patient is infused with the autologous peripheral blood progenitor cells, the patient receives chemotherapy over a period of 96 hours (4 days), with the following chemotherapy agents:

1. Cyclophosphamide in a total dosage of 6 g/m$^2$ (1.5 g/m 2/day for 4 days) is given via continuous intravenous infusion at 500 mg/m$^2$ in 1,000 ml normal saline every 8 hours.
2. Thiotepa in a total dosage of 500 mg/m$^2$/day for 4 days) is given via continuous intravenous infusion at 125 mg/m$^2$ in 1,000 ml normal saline every 24 hours.
3. Carboplatin in a total dosage of 1,800 mg/m$^2$ (200 mg/m$^2$/day for 4 days) is given via continuous intravenous infusion at 200 mg/m$^2$ in 1,000 ml of 5% dextrose in water every 24 hours.

The patient also receives 500 mg of mesna in 50 ml normal saline IV over 15 minutes every 4 hours for 6 days (144 hours), beginning with the first dose of cyclophosphamide.

At least 72 hours after the completion of the chemotherapy, the mesenchymal stem cells are harvested from tissue culture flasks. Cells are collected using bovine trypsin (which is deactivated with soybean trypsin inhibitor), suspended at $10\times10^6$ cells/ml in TC199 containing 1% human serum albumin (infusion medium), washed twice in infusion medium, resuspended at approximately $10^6$ cells/ml, and injected slowly intravenously over 15 minutes to provide a total dosage of from 10 to about $5\times10^6$ cells.

The day after the patient receives the mesenchymal stem cells, the frozen autologous peripheral blood progenitor cells are removed from the liquid nitrogen refrigerator, transported to the patient in liquid nitrogen, submersed in a 37° C. to 40° C. sterile water bath, and infused rapidly intravenously without additional filtering or washing steps. GM-CSF in an amount of 250 $\mu$g/m$^2$ then is given as a daily subcutaneous injection, beginning 3 hours after completion of the autologous blood progenitor cell infusion. The GM-CSF is given daily until the peripheral blood neutrophil count exceeds 1,000 L for three consecutive days.

It is to be understood, however, that the scope of the present invention is not to be limited to the specific embodiments described above. The invention may be practiced other than as particularly described and still be within the scope of the accompanying claims.

What is claimed is:

1. A method for enhancing engraftment of hematopoietic progenitor cells in an individual in need thereof which comprises administering to said individual (i) isolated, homogeneous mesenchymal stem cells and (ii) hematopoietic progenitor cells, wherein said mesenchymal stem cells are administered in an amount effective to promote engraftment of said hematopoietic progenitor cells in said individual.

2. The method of claim 1 wherein the mesenchymal stem cells are administered by intravenous injection or by injection directly to the site of intended activity.

3. The method of claim 1 wherein at least one of (i) the mesenchymal stem cells and (ii) the hematopoietic progenitor cells is administered intravenously.

4. The method of claim 1 wherein at least one of (i) the mesenchymal stem cells and (ii) the hematopoietic progenitor cells is administered by injection directly to the site of intended activity.

5. The method of claim 1 wherein the mesenchymal stem cells are autologous.

6. The method of claim 1 wherein the mesenchymal stem cell preparation is administered concurrently with the hematopoietic progenitor cells.

7. The method of claim 6 wherein the mesenchymal stem cells are introduced into said individual in a cell suspension also containing hematopoietic progenitor cells.

8. The method of claim 1 wherein the mesenchymal stem cell preparation is administered to the individual prior to administration of the hematopoietic progenitor cells.

* * * * *